(12) United States Patent
Brotman et al.

(10) Patent No.: US 11,690,657 B2
(45) Date of Patent: Jul. 4, 2023

(54) REDUCTION INSTRUMENTS AND METHODS

(71) Applicant: NuVasive, Inc., San Diego, CA (US)

(72) Inventors: Michael Brotman, San Diego, CA (US); Gregory M. Mundis, Jr., San Diego, CA (US)

(73) Assignee: NuVasive, Inc., San Diego, CA (US)

(*) Notice: Subject to any disclaimer, the term of this patent is extended or adjusted under 35 U.S.C. 154(b) by 394 days.

(21) Appl. No.: 16/922,208

(22) Filed: Jul. 7, 2020

(65) Prior Publication Data

US 2020/0330138 A1 Oct. 22, 2020

Related U.S. Application Data

(63) Continuation of application No. 16/132,133, filed on Sep. 14, 2018, now Pat. No. 10,743,921, which is a continuation of application No. 15/183,762, filed on Jun. 15, 2016, now Pat. No. 10,123,829.

(60) Provisional application No. 62/175,624, filed on Jun. 15, 2015.

(51) Int. Cl.
| A61B 17/80 | (2006.01) |
| A61B 17/70 | (2006.01) |
| A61B 17/17 | (2006.01) |
| A61B 17/56 | (2006.01) |

(52) U.S. Cl.
CPC ...... *A61B 17/8019* (2013.01); *A61B 17/1728* (2013.01); *A61B 17/7059* (2013.01); *A61B 17/7079* (2013.01); *A61B 2017/564* (2013.01)

(58) Field of Classification Search
CPC ............ A61B 17/1728; A61B 17/1615; A61B 2017/90; A61B 2017/681
See application file for complete search history.

(56) References Cited

U.S. PATENT DOCUMENTS

| 4,611,581 A | 9/1986 | Steffee |
| 4,696,290 A | 9/1987 | Steffee |
| 5,423,826 A | 6/1995 | Coates et al. |
| 5,601,556 A | 2/1997 | Pisharodi |
| 5,653,761 A | 8/1997 | Pisharodi |
| 5,658,336 A | 8/1997 | Pisharodi |
| 5,697,977 A | 12/1997 | Pisharodi |
| 5,782,831 A | 7/1998 | Sherman |
| 5,893,890 A | 4/1999 | Pisharodi |
| 6,093,207 A | 7/2000 | Pisharodi |
| 6,193,721 B1 | 2/2001 | Michelson |
| 6,309,421 B1 | 10/2001 | Pisharodi |
| 6,440,133 B1 | 8/2002 | Beale |
| 6,533,791 B1 | 3/2003 | Betz |
| 6,790,209 B2 | 9/2004 | Beale |
| 6,896,676 B2 | 5/2005 | Zubok |
| 6,908,484 B2 | 6/2005 | Zubok |
| 6,972,037 B2 | 12/2005 | Zubok |

(Continued)

FOREIGN PATENT DOCUMENTS

| CN | 201760455 U | 3/2011 |
| IN | 1998CA01282 | 3/2005 |

*Primary Examiner* — Eduardo C Robert
*Assistant Examiner* — Tara Rose E Carter
(74) *Attorney, Agent, or Firm* — Hoffman Warnick LLC

(57) ABSTRACT

The present subject disclosure provides a novel design for devices and methods for straightening a curved spine by using a reduction tool to move the spine with respect to an attached bone plate.

20 Claims, 7 Drawing Sheets

(56) References Cited

U.S. PATENT DOCUMENTS

| | | |
|---|---|---|
| 6,972,038 B2 | 12/2005 | Zubok |
| 6,994,728 B2 | 2/2006 | Zubok |
| 6,994,729 B2 | 2/2006 | Zubok |
| 6,997,954 B2 | 2/2006 | Zubok |
| 6,997,955 B2 | 2/2006 | Zubok |
| 7,160,300 B2 | 1/2007 | Jackson |
| 7,198,643 B2 | 4/2007 | Zubok |
| 7,621,918 B2 | 11/2009 | Jackson |
| 7,662,182 B2 | 2/2010 | Zubok |
| 7,744,649 B2 | 6/2010 | Moore |
| 7,811,312 B2 | 10/2010 | Stevens |
| 7,879,095 B2 | 2/2011 | Pisharodi |
| 7,914,562 B2 | 3/2011 | Zielinski |
| 7,931,654 B2 | 4/2011 | Jones |
| 7,959,677 B2 | 6/2011 | Landry |
| 8,043,338 B2 | 10/2011 | Dant |
| 8,100,915 B2 | 1/2012 | Jackson |
| 8,133,230 B2 | 3/2012 | Stevens |
| 8,162,948 B2 | 4/2012 | Jackson |
| 8,172,854 B2 * | 5/2012 | Blain .............. A61B 17/1728 606/86 A |
| 8,216,313 B2 | 7/2012 | Moore |
| 8,231,628 B2 | 7/2012 | Zubok |
| 8,283,753 B2 | 10/2012 | Okamura |
| 8,287,546 B2 | 10/2012 | King |
| 8,377,067 B2 | 2/2013 | Jackson |
| 8,377,098 B2 | 2/2013 | Landry |
| 8,377,104 B2 | 2/2013 | Jones |
| 8,377,130 B2 | 2/2013 | Moore |
| 8,388,688 B2 | 3/2013 | Moore |
| 8,394,109 B2 | 3/2013 | Hutton |
| 8,414,626 B2 | 4/2013 | Zielinski |
| 8,435,297 B2 | 5/2013 | Zubok |
| RE44,296 E | 6/2013 | Beale |
| 8,469,960 B2 | 6/2013 | Hutton |
| 8,480,740 B2 | 7/2013 | Pisharodi |
| 8,556,975 B2 | 10/2013 | Ciupik |
| 8,575,721 B2 | 11/2013 | Okamura |
| 8,591,515 B2 | 11/2013 | Jackson |
| 8,597,358 B2 | 12/2013 | Landry |
| 8,641,742 B2 | 2/2014 | Stevens |
| RE44,813 E | 3/2014 | Beale |
| 8,679,128 B2 | 3/2014 | Seelig |
| 8,795,283 B2 | 8/2014 | Petit |
| 8,814,914 B2 | 8/2014 | Miller |
| 8,821,502 B2 | 9/2014 | Gleeson |
| 8,845,733 B2 | 9/2014 | O'Neil |
| 8,876,835 B2 | 11/2014 | Petit |
| 8,900,238 B2 | 12/2014 | Iott |
| 8,936,599 B2 | 1/2015 | Glazer |
| 8,936,640 B2 | 1/2015 | Zubok |
| 8,940,022 B2 | 1/2015 | Landry |
| 8,961,608 B2 | 2/2015 | Zubok |
| 9,028,552 B2 | 5/2015 | Zubok |
| 9,055,978 B2 | 6/2015 | Jackson |
| 9,060,825 B2 | 6/2015 | Hutton |
| 9,066,763 B2 | 6/2015 | Khoo |
| 9,066,811 B2 | 6/2015 | Landry |
| 9,084,648 B2 | 7/2015 | Seelig |
| 9,101,414 B2 | 8/2015 | King |
| 9,101,415 B2 | 8/2015 | Jackson |
| 9,125,703 B2 | 9/2015 | McClintock |
| 9,161,788 B2 | 10/2015 | Daubs |
| 9,173,682 B2 | 11/2015 | Jackson |
| 9,198,771 B2 | 12/2015 | Ciupik |
| 9,204,906 B2 | 12/2015 | Cannestra |
| 9,204,909 B2 | 12/2015 | Rezach |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 9,282,979 B2 | 3/2016 | O'Neil |
| 9,289,251 B2 | 3/2016 | Leroux |
| 9,295,494 B2 | 3/2016 | Strauss |
| 9,320,550 B2 | 4/2016 | Hutton |
| 9,445,849 B2 | 9/2016 | King |
| 9,572,589 B2 | 2/2017 | Knape et al. |
| 10,123,829 B1 * | 11/2018 | Brotman ............ A61B 17/7079 |
| 10,743,921 B2 * | 8/2020 | Brotman ............ A61B 17/7059 |
| 2004/0073214 A1 | 4/2004 | Mehdizadeh |
| 2005/0240270 A1 | 10/2005 | Zubok |
| 2006/0184178 A1 | 8/2006 | Jackson |
| 2006/0293680 A1 | 12/2006 | Jackson |
| 2007/0093834 A1 | 4/2007 | Stevens |
| 2007/0123989 A1 | 5/2007 | Gfeller |
| 2008/0015601 A1 | 1/2008 | Castro |
| 2009/0088803 A1 | 4/2009 | Justis |
| 2010/0130981 A1 | 5/2010 | Richards |
| 2011/0319899 A1 | 12/2011 | O'Neil |
| 2011/0319998 A1 | 12/2011 | O'Neil |
| 2011/0320000 A1 | 12/2011 | O'Neil |
| 2012/0271358 A1 | 10/2012 | Stevens |
| 2013/0012999 A1 | 1/2013 | Petit |
| 2013/0018418 A1 | 1/2013 | Petit |
| 2013/0066385 A1 | 3/2013 | Benoist |
| 2013/0123865 A1 | 5/2013 | Moore |
| 2013/0245691 A1 | 9/2013 | Hutton |
| 2013/0274804 A1 | 10/2013 | Hutton |
| 2013/0325071 A1 | 12/2013 | Niemiec |
| 2014/0012321 A1 | 1/2014 | Hutton |
| 2014/0031872 A1 | 1/2014 | Jackson |
| 2014/0031873 A1 | 1/2014 | Jackson |
| 2014/0074106 A1 | 3/2014 | Shin |
| 2014/0074171 A1 | 3/2014 | Hutton |
| 2014/0222090 A1 | 8/2014 | Jackson |
| 2014/0277167 A1 | 9/2014 | Hutton |
| 2014/0277168 A1 | 9/2014 | Hutton |
| 2015/0032212 A1 | 1/2015 | O'Neil |
| 2015/0051653 A1 | 2/2015 | Cryder |
| 2015/0057713 A1 | 2/2015 | Iott |
| 2015/0066042 A1 | 3/2015 | Cummins |
| 2015/0081021 A1 | 3/2015 | Ciupik |
| 2015/0164494 A1 | 6/2015 | Glazer |
| 2015/0164651 A1 | 6/2015 | Zubok |
| 2015/0216568 A1 | 8/2015 | Sanpera |
| 2015/0230834 A1 | 8/2015 | Cannestra |
| 2015/0272631 A1 | 10/2015 | Jackson |
| 2015/0272632 A1 | 10/2015 | Seelig |
| 2015/0351814 A1 | 12/2015 | McClintock |
| 2016/0000479 A1 | 1/2016 | Daubs |
| 2016/0015433 A1 | 1/2016 | Jackson |
| 2016/0022328 A1 | 1/2016 | Rezach |
| 2016/0038306 A1 | 2/2016 | O'Neil |
| 2016/0120658 A1 | 5/2016 | Zubok |
| 2016/0256195 A1 | 9/2016 | Boachie-Adjei |

* cited by examiner

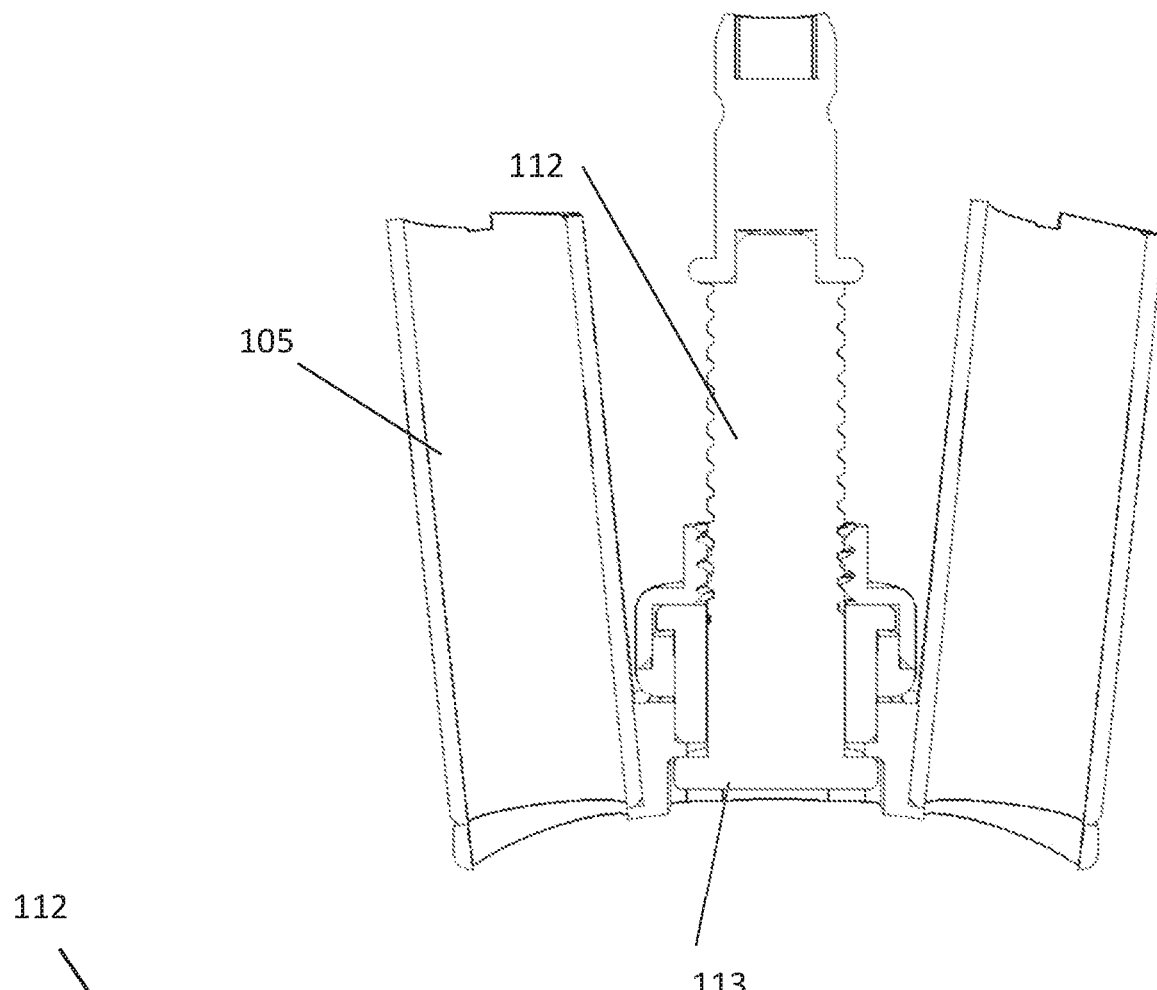
FIG. 3
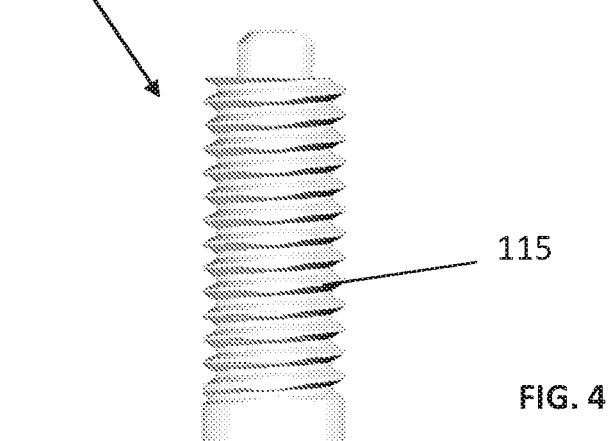
FIG. 4
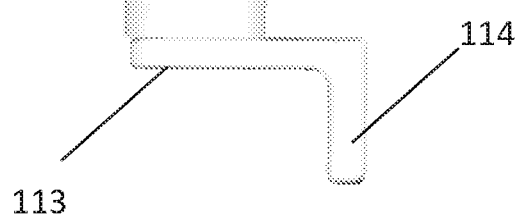

REDUCTION INSTRUMENTS AND METHODS

This application is a continuation of Ser. No. 16/132,133 filed Sep. 14, 2018, which is a continuation application of Ser. No. 15/183,762 filed on Jun. 15, 2016, which claims priority to U.S. Provisional Patent Application Ser. No. 62/175,624, filed on Jun. 15, 2015, the entire contents of which are incorporated by reference as if set forth herein in their entireties.

TECHNICAL FIELD

The subject disclosure relates generally to spinal devices and methods of surgery. Specifically, the subject disclosure relates to reduction instruments and methods for use.

BACKGROUND OF THE SUBJECT DISCLOSURE

Back problems are one of the most common and debilitating occurrences in people of all ethnicities. In the United States alone, over 500,000 spine lumbar and cervical fusion procedures are performed each year. One of the causes of back pain and disability results from the rupture or degeneration of one or ore intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF) and lateral lumbar interbody fusion (XLIF) procedures are two of the techniques that spine surgeons use to access the portions of the spine to be repaired or replaced. Replacement of injured or deteriorated spinal bone with artificial implants requires a balance of knowledge of the mechanisms of the stresses inherent in the spine, as well as the biological properties of the body in response to the devices. Spinal deformities typically need some sort of alignment device or technique to correct the deformity.

Further, the size, configuration, and placement of a correction device require precision positioning and handling by a skilled surgeon.

SUMMARY OF THE SUBJECT DISCLOSURE

The present subject disclosure provides a description of novel reduction devices and methods which work with spinal plates to provide correction of a particular segment of the spine, depending on the needs or the functionality of the particular placement of the device.

In one exemplary embodiment, the subject matter is a spinal reduction device. The device includes a base having a longitudinal axis; a vertical post positioned substantially centrally on the longitudinal axis of the base, wherein the vertical post has a longitudinal axis which is substantially perpendicular to the longitudinal axis of the base; a translating nut adapted to translate along the longitudinal axis of the vertical post; and at least one guide, said at least one guide positioned on one end of the base, wherein the guide has a longitudinal axis which is generally perpendicular to the longitudinal axis of the base. According to one aspect, the guide is positioned relative to the base such that it angled medially from 0 to 10 degrees. According to another aspect, the guide is positioned relative to the base at a 6° angle.

In another exemplary embodiment, the subject matter is a spinal reduction device. The device includes a base having a longitudinal axis; a vertical post positioned substantially centrally on the longitudinal axis of the base; a translating nut adapted to translate along a longitudinal axis of the vertical post; and at least one guide, said guide positioned on one end of the base, each guide having a distal end that engages with the base; and a proximal end that has teeth which are adapted to engage with a head of a tap and prevent it from further rotation when the tap shaft is inserted a certain distance into an interior of the guide.

In yet another exemplary embodiment, the subject matter is a method of reducing a spine. The method includes positioning a bone plate adjacent to an anterior spinal column; attaching a reduction instrument to the bone plate; driving temporary taps through the guides and into the spine until the taps bottom out on teeth on proximal ends of the guides; using a driver to spin a translation nut and translate the reduction instrument away from the bone plate; and replacing the taps one at a time with bone screws.

BRIEF DESCRIPTION OF THE DRAWINGS

Many advantages of the present subject disclosure will be apparent to those skilled in the art with a reading of this specification in conjunction with the attached drawings, which include:

FIG. 3 shows a mid-planar cut of the front view of a reduction device, according to an exemplary embodiment of the subject disclosure.

FIG. 4 shows a side view of the pusher assembly portion of the reduction device, according to an exemplary embodiment of the subject disclosure.

DETAILED DESCRIPTION OF THE SUBJECT DISCLOSURE

Figure 1:
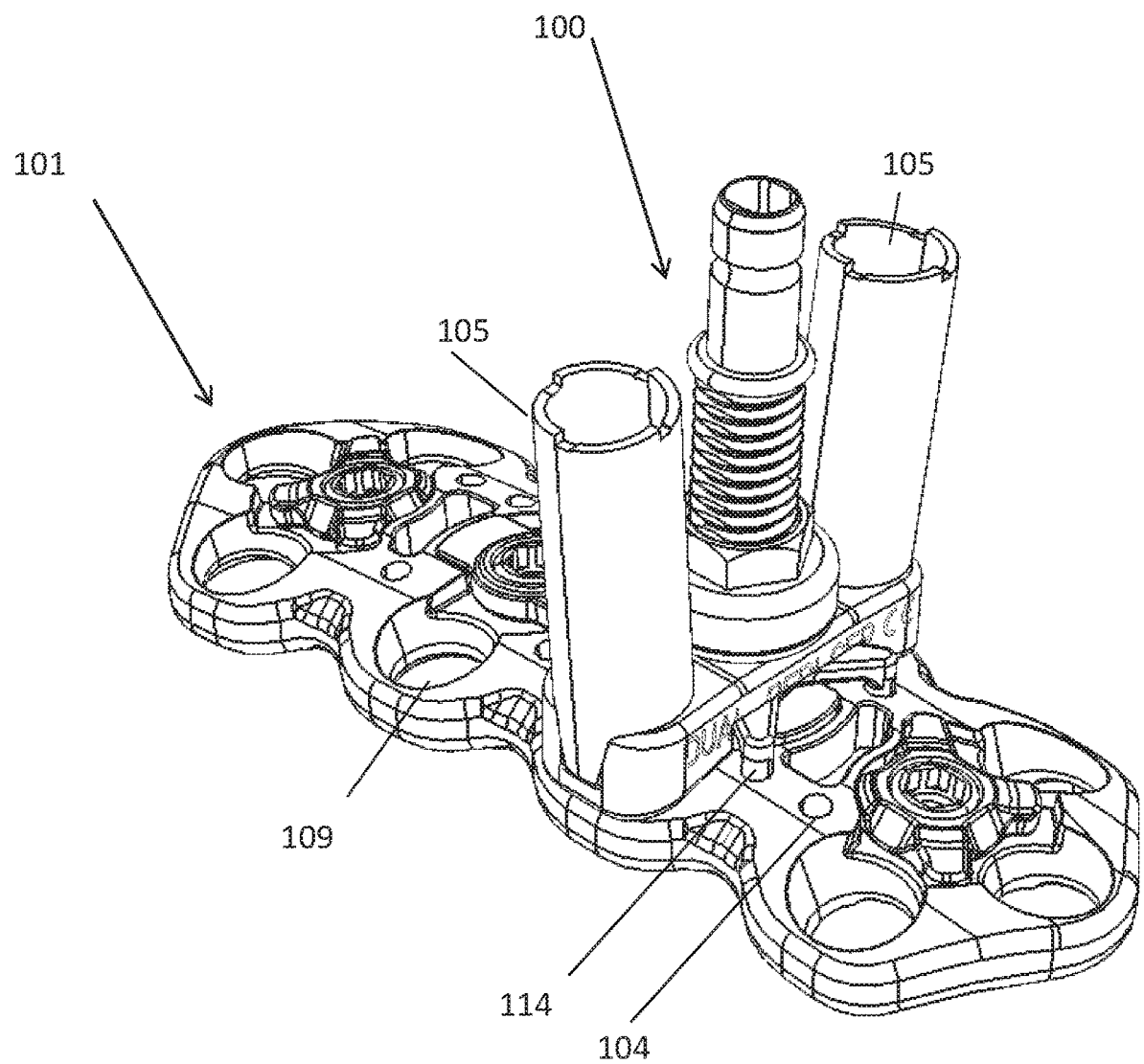
FIG. 1 shows a perspective view of a reduction device in connection with a spinal bone plate, according to an exemplary embodiment of the subject disclosure.

The following detailed description references specific embodiments of the subject disclosure and accompanying figures, including the respective best modes for carrying out each embodiment. It shall be understood that these illustrations are by way of example and not by way of limitation.

Illustrative embodiments of the subject disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The versatile reduction device and related methods disclosed herein boast a variety of novel features and components that warrant patent protection, both individually and in combination.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The reduction instrument described herein has many uses, and in the embodiment presented, is configured for use in spine surgery to aid a surgeon in mechanically correcting the sagittal alignment of a spine during application of a bone plate to the anterior column of the spine. However, the instrument may be used in other geometries and positions as well to correct the alignment of the spine. In general, a combination of elements defines the reduction instrument, including (1) a reducer, (2) a reduction driver, and (3) reduction taps.

Figure 2:
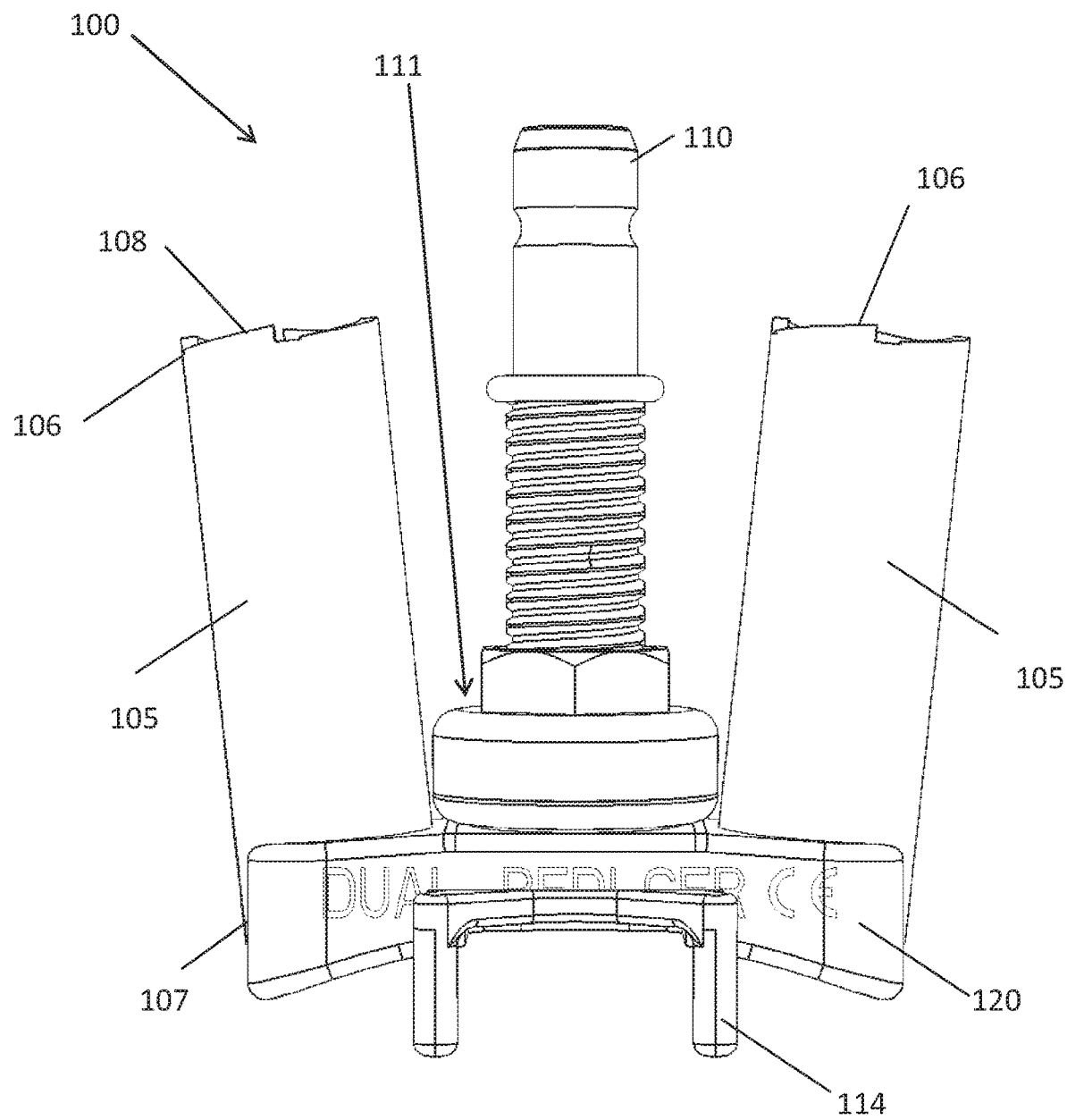
FIG. 2 shows a front view of a reduction device, according to an exemplary embodiment of the subject disclosure.
Figure 5:
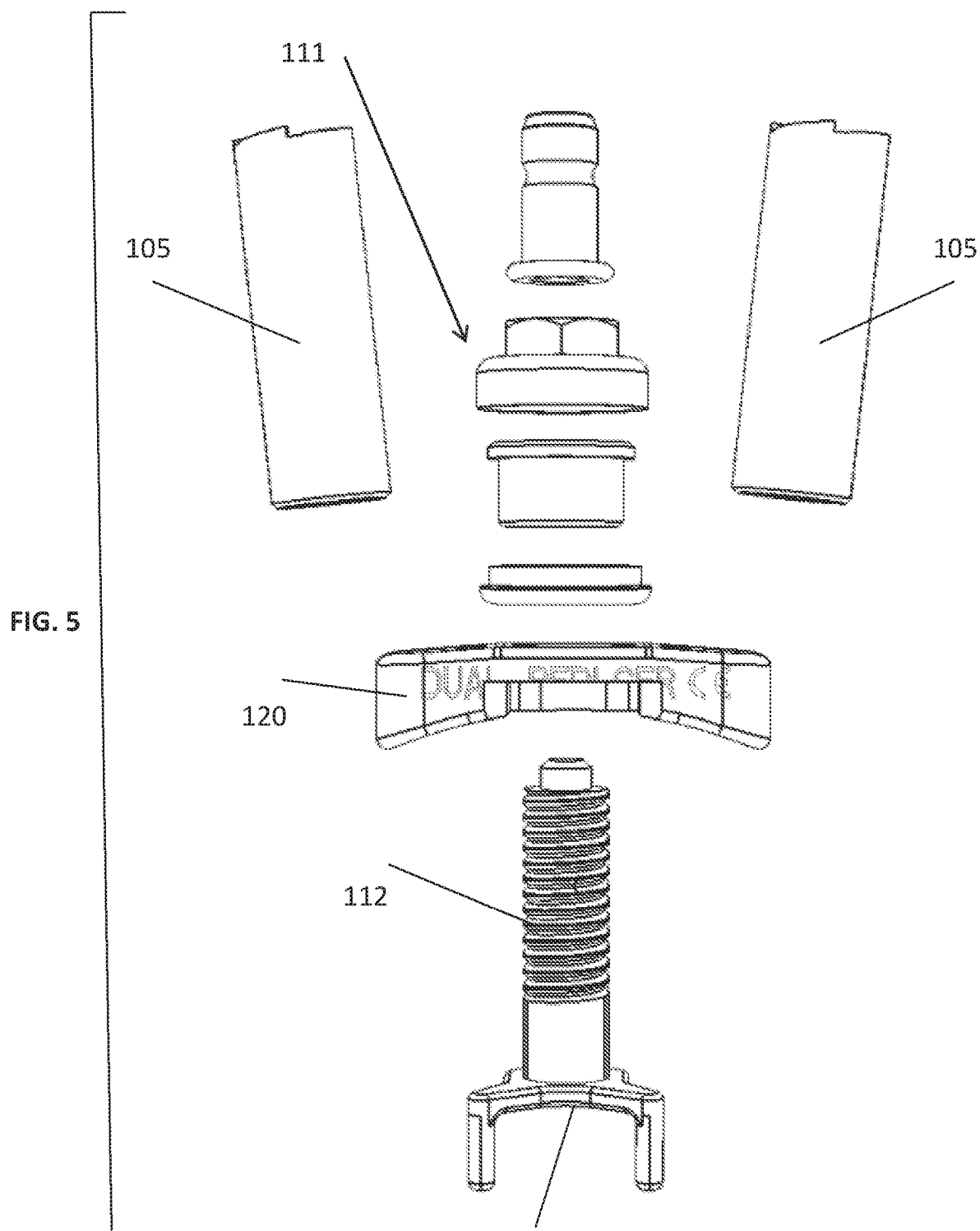
FIG. 5 shows an exploded view of a reduction device, according to an exemplary embodiment of the subject disclosure.

According to an exemplary embodiment shown in FIG. 2, a reducer device 100 includes first and second guides 105 and a pusher element 110 coupled to a base 120. The reducer 100 further includes a plate attachment element 114 to fix the reducer instrument to the bone plate 101, such as an anterior spinal plate, as shown in FIG. 1. In the embodiments shown in FIGS. 1-5, the plate attachment element 114 has two prongs which mate with corresponding apertures 104 in the bone plate 101 body. However, more than two prongs may also be used to provide for stable attachment of the reduction instrument 100 to the bone plate 101. Once the prongs of the plate attachment element 114 are mated with the corresponding apertures 104 of the plate 101, the guides 105 allow for symmetric reduction of a given vertebral level by using both lateral bone screw holes 109 on the bone plate, thereby distributing the load between two screw holes 109, as shown in FIG. 1. As shown in FIG. 1, the screw holes 109 are arranged as a linear array on the outer edges of the plate 101 such that the reduction instrument 100 is mated onto the plate 101 surface from one side to another side. The reduction instrument 100 is essentially positioned perpendicular to the longitudinal axis of the plate 101 shown in FIG. 1. Although illustrated with a pair of guides 105 throughout the disclosure, it is contemplated that the reducer could have a single guide, a pair of guides as shown, or three or more guides to accommodate the number of holes on an anterior plate at the vertebral level being treated.

As shown best in FIG. 1, the guides 105 are hollow, having a distal end 107 where the guides 105 engage the base 120 and an opposite proximal end 106. The proximal end 106 includes teeth 108 that are configured to engage with a corresponding structure in the head of a reduction tap 151 to inhibit further rotation of the tap 151 and thereby prevent stripping, or to prevent the distal end 152 of the tap to penetrate too far into the bony material 155. The pusher 112 includes a threaded shaft 115 configured to guide a translation nut 111 during use. The reduction taps 151 are dimensioned to have a smaller diameter at their distal ends 152 and throughout than the bone screws 156 that will ultimately be used to fix the plate 101 to the spine 155. According to an exemplary embodiment, the reduction taps 151 have a smaller diameter than the bone screws 156 but have the same thread form in their distal regions 152. This assists in setting a guide hole into the bony material 155 by the tap 151 without over-boring the bony material 155.

The reduction driver 153 is configured to be inserted over the threaded shaft 115 of the pusher 112 to engage the translation nut 111. The translation nut 111 may be a hexagonal nut, which translates vertically with respect to the longitudinal axis of the pusher 112, mates with a female hexagonal internal configuration within the distal end of the reduction driver 153 to allow for rotation of the translation nut, resulting in up/down motion of the nut 11 over the threaded portion 115 of the pusher 112. In use, the driver 153 will hold the plate 101 in place while pulling the taps 151 in a proximal direction away from the plate 101.

Figure 6:
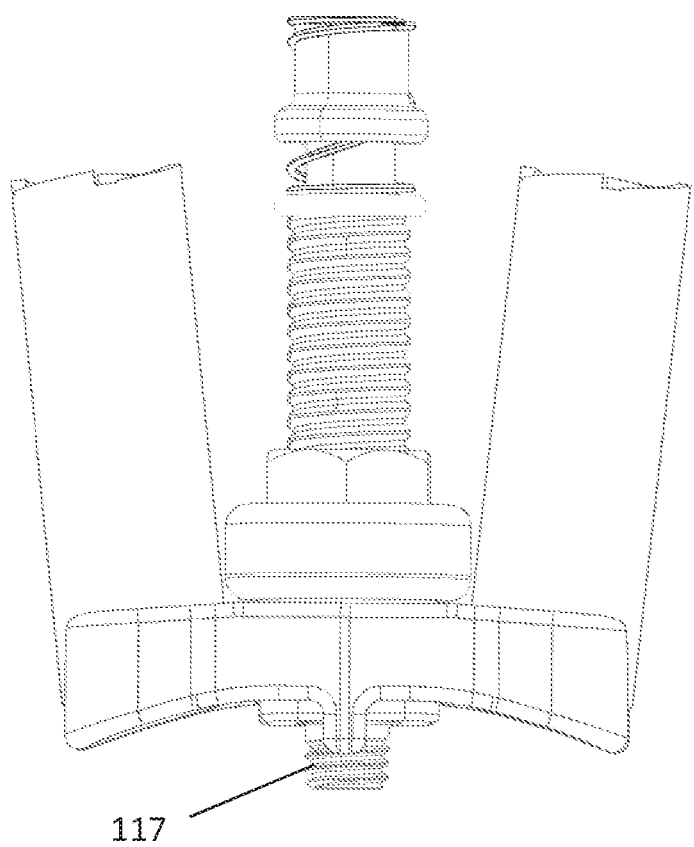
FIG. 6 shows a front view of a reduction device, according to another exemplary embodiment of the subject disclosure.
Figure 7:
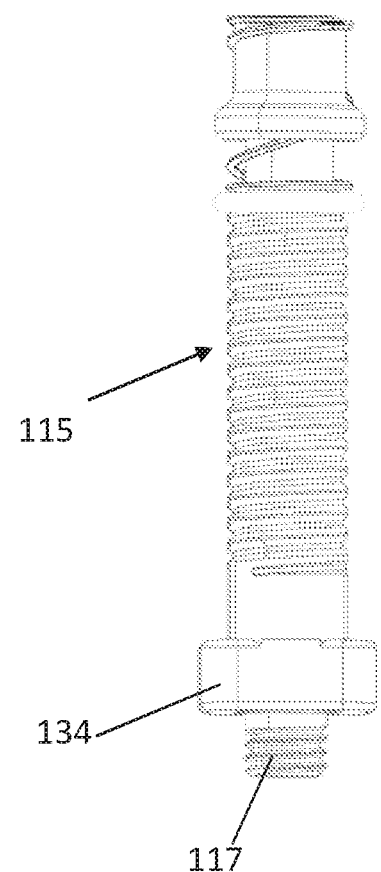
FIG. 7 shows a front view of the pusher assembly portion of the reduction device, according to another exemplary embodiment of the subject disclosure.
Figure 8:
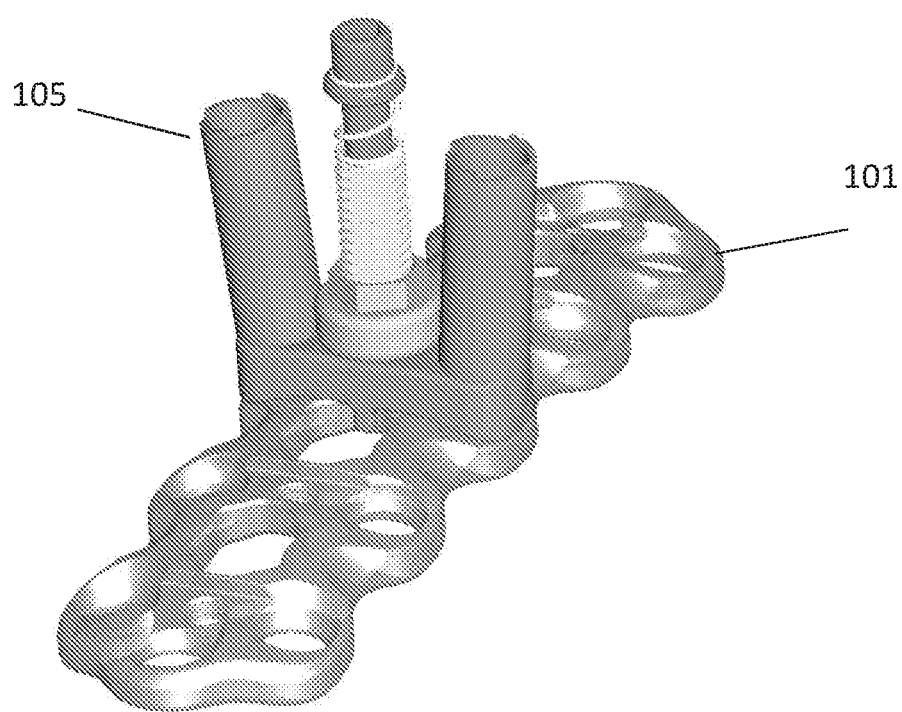
FIG. 8 shows a perspective view of a reduction device in connection with a spinal bone plate, according to an exemplary embodiment of the subject disclosure.
Figure 9:
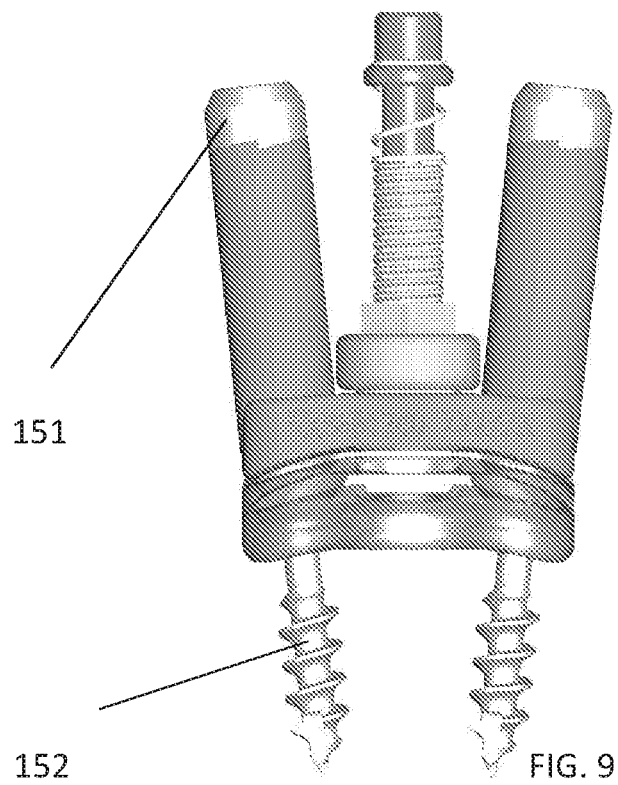
FIG. 9 shows a front view of a reduction device with reduction taps in place, according to an exemplary embodiment of the subject disclosure.
Figure 10A:
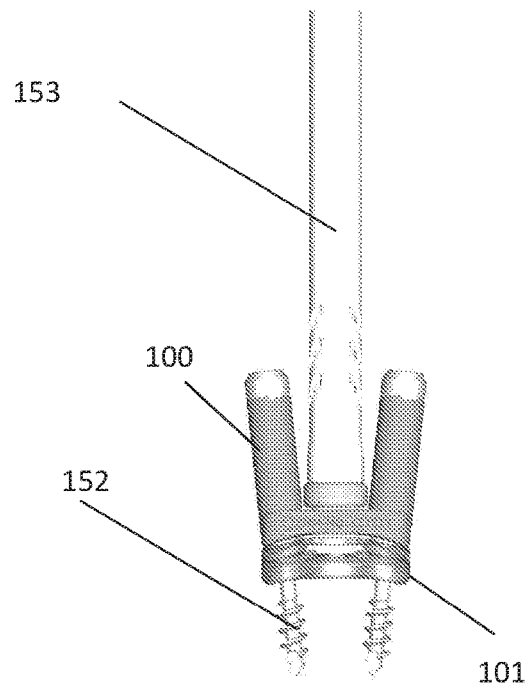
FIG. 10A shows a front view of a reduction device with reduction taps in place and reduction driver engaged in an initial step, according to an exemplary embodiment of the subject disclosure.
Figure 10B:
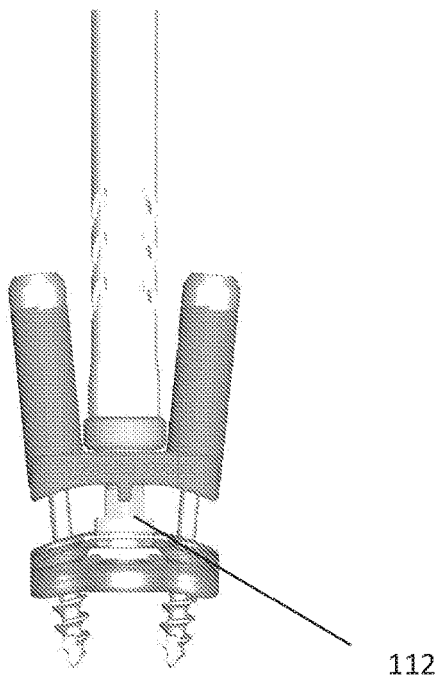
FIG. 10B shows a front view of a reduction device with reduction taps in place and reduction driver engaged to place plate in a desired position, according to an exemplary embodiment of the subject disclosure.
Figure 11A:
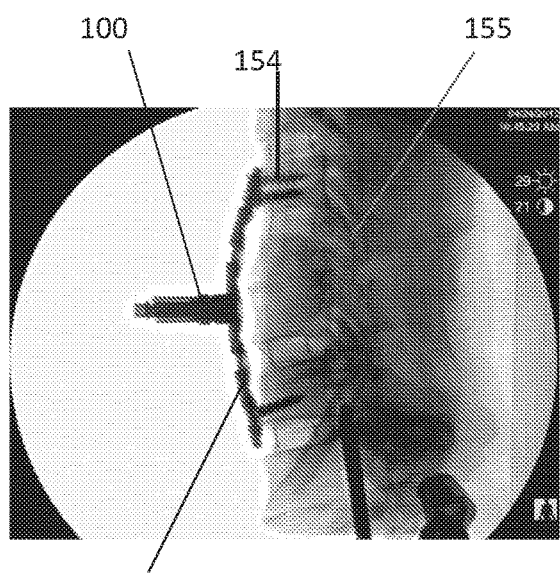
FIG. 11A shows a side planar cut view of a reduction device with bone screws in place in an initial step, according to an exemplary embodiment of the subject disclosure.
Figure 11B:
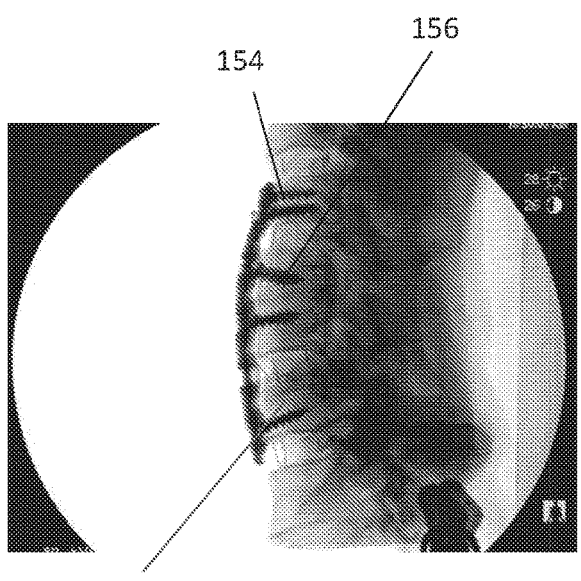
FIG. 11B shows a side planar cut view of a bone plate in a desired position, according to an exemplary embodiment of the subject disclosure.

FIGS. 6 and 7 illustrate an alternative embodiment of the reducer instrument 100. The reducer 100 according to this embodiment has all the same features as the exemplary embodiment shown in FIG. 1, but has an alternative plate attachment feature 117. According to the embodiment of FIGS. 6 & 7, the plate attachment member 117 is a threaded post that is configured to engage a complementary threaded hole in a central longitudinal position of the anterior bone plate 101. Once the reducer instrument 100 is anchored to the plate 101, the reducer of this embodiment is used in the same way as described with respect to the embodiment of FIGS. 1-5.

In use, and as shown in FIGS. 8-11B, an anterior bone plate 101 is positioned adjacent to the anterior column of a spine 155 aligning bone screw holes with vertebral bodies. According to one exemplary embodiment, bone screws are placed at the cranial and caudal ends of the plate before reduction occurs. In this exemplary embodiment, one set of bone screws 154 engages the superior-most set of screw holes at the superior (cranial end) end of the plate 101 and another set of bone screws 154 engages the inferior-most (caudal end) set of screw holes at the inferior end of the plate 101. Other embodiments are contemplated that do not require the bone plate to be fixed to the spine at the cranial and/or caudal ends prior to the reduction step.

The reducer 100 is then attached to an anterior bone plate 101 adjacent a pair of screw holes 109 located on a central portion of the plate 101, i.e., in between the superior and inferior sets of screw holes. Proper attachment of the reducer 100 to the plate 101 is achieved by coupling the plate attachment member 114 of the reducer 100 to the bone plate 101 such that the central longitudinal apertures of the guides 105 are aligned with the screw holes 109 on the plate 100, as shown in FIG. 1.

Once the reduction instrument 100 is docked to the plate 101, reduction taps 151 are inserted through the guides 105 then through the holes 109 of the bone plate 101, until the head of the reduction tap 151 bottoms out on and engages the teeth 108 on the proximal end 106 of the guide 105.

After the taps 151 are in place, a driver 153 is attached to the reducer 100 over the threaded shaft 115 of the pusher 112 and engaging the translation nut 111. The translation nut 111 is rotated, causing the nut 111 to translate along the threaded shaft 115 of the pusher 112. This causes the distal end 113 of the pusher 112 to push against the plate 101 in a first direction while pulling the heads of the reduction tap 151 in a second, opposite direction. In other words, rotation of the driver 153 terns to pull the reduction instrument 100 upwards, which then in turn pulls up on the reduction taps 151 because the guides 105 push the heads of the taps 151 upwards during the movement. This action causes the vertebral body 155 coupled to the reduction taps 151 to be drawn closer to the plate 101 while the plate 101 remains stationary, thereby changing the alignment of the spinal segment being treated as the vertebral body 155 is brought in closer to the plate 101.

When the desired alignment of the vertebral body 155 is achieved, one reduction tap 151 is replaced by a first bone screw 156 by inserting the screw 156 through the central longitudinal aperture of the guide 105 and through the bone plate 100. After the first bone screw 156 is place, the other reduction tap is replaced by a second bone screw. This method is repeated for additional levels that require reduction.

The reduction instrument 100 is configured such that a plurality of reduction instruments can be employed simultaneously at a plurality of screw hole 109 locations on the plate 101. When a plurality of reduction instruments 100 is employed simultaneously, adjustments can be made in increments sequentially at each level being reduced until the desired alignment is achieved. For example, if two reduction instruments 100 are used simultaneously, a user could adjust the alignment of the first vertebral body, then adjust the alignment of the second vertebral body, then go back and adjust the alignment of the first vertebral body further, and so on. In an alternative embodiment, each vertebral body being realigned could be lagged to the plate to the desired level before adjacent levels are treated.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A spinal reduction device, comprising:
   a base comprising an upper surface, a bottom plate-facing surface, a first side, a second side, a first end, and a second end;
   a vertical post coupled to the base and extending upwardly from the upper surface of the base, wherein the vertical post comprises an external thread;
   a translation nut configured to threadably engage the external thread of the vertical post;
   a plate attachment element extending away from the first side of the base in a direction away from the second side of the base and generally parallel to the bottom plate-facing surface of the base, the plate attachment element comprising a distal portion adapted to be visible to a user when viewed from above the base, the plate attachment element being adapted to engage with one or more attachment apertures in a bone plate; and
   a first guide extending upwards from the base adjacent the first end thereof, the first guide comprising a first guide passage with a longitudinal axis.

2. The spinal reduction device of claim 1, wherein the plate attachment element further comprises at least two prongs extending away and downward from the distal portion of the plate attachment element, each prong adapted to engage the one or more attachment apertures in the bone plate.

3. The spinal reduction device of claim 2, wherein the distal portion of the plate attachment element comprises a first arm and a second arm, wherein a first prong of the at least two prongs extends downwardly from a distal end of the first arm, and a second prong of the at least two prongs extends downwardly from a distal end of the second arm.

4. The spinal reduction device of claim 2, wherein when the at least two prongs are engaged with corresponding attachment apertures in the bone plate, the first guide passage is aligned such that its longitudinal axis extends directly through a first screw hole positioned in the bone plate.

5. The spinal reduction device of claim 4, wherein the first guide is configured to receive a reduction tap in the first guide passage to position the reduction tap in the first screw hole of the bone plate.

6. The spinal reduction device of claim 5, wherein the first guide comprises a proximal end having teeth configured to engage a head of the reduction tap.

7. The spinal reduction device of claim 1, further comprising a second guide extending upwards from the base adjacent the second end thereof, the second guide comprising a second guide passage with a longitudinal axis.

8. The spinal reduction device of claim 1, wherein the translation nut comprises an outer geometry configured to matingly engage with a driver to rotate the translation nut, thereby translating the translation nut along the vertical post.

9. A system, comprising:
a bone plate configured to couple to a spine in a patient, the bone plate comprising one or more attachment apertures and a bone screw hole extending therethrough; and
a spinal reduction device configured to couple to the bone plate, the spinal reduction device comprising:
a base having an upper surface, a bottom plate-facing surface, a first side, a second side, a first end, and a second end;
a vertical post coupled to the base and extending upward from the upper surface of the base, wherein the vertical post comprises an external thread;
a translation nut configured to threadably engage the external thread of the vertical post;
a plate attachment element coupled to the bottom plate-facing surface of the base and configured to engage the attachment aperture of the bone plate, wherein the plate attachment element comprises a distal portion adapted to be visible to a user when viewed from above the base; and
a first guide extending upwards from the base adjacent the first end thereof, wherein the first guide comprises a first guide passage having a longitudinal axis.

10. The system of claim 9, further comprising a reduction tap configured to be received in the bone screw hole of the bone plate.

11. The system of claim 10, wherein the first guide is configured to receive the reduction tap in the first guide passage to position the reduction tap in the bone screw hole.

12. The system of claim 11, wherein the first guide comprises a proximal end having teeth configured to engage a head of the reduction tap and inhibit movement of the reduction tap along the longitudinal axis of the first guide passage.

13. The system of claim 9, further comprising a driver configured to rotatably engage the translation nut thereby translating the translation nut along the external thread of the vertical post.

14. The system of claim 13, wherein the translation nut comprises a hexagonal outer geometry configured to matingly engage with the driver.

15. The system of claim 9, wherein the spinal reduction device comprises a second guide extending upwards from the base adjacent the second end thereof, the second guide comprising a second guide passage having a longitudinal axis.

16. The system of claim 9, wherein the plate attachment element comprises a first prong and a second prong that extend away and downward from the distal portion of the plate attachment element, wherein the first and second prongs are configured to engage the one or more attachment apertures in the bone plate.

17. The system of claim 16, wherein the distal portion of the plate attachment element comprises a first arm and a second arm, wherein the first prong extends from the first arm and the second prong extends from the second arm.

18. The system of claim 16, wherein, when the first and second prongs are engaged with corresponding attachment apertures in the bone plate, the first guide passage aligns with the first screw hole of the bone plate.

19. The system of claim 9, further comprising a bone screw configured to couple the bone plate to the spine, wherein the bone screw hole of the bone plate is dimensioned to receive the bone screw therein.

20. The system of claim 9, wherein the plate attachment element is configured to extend away from the first side of the base in a direction away from the second side of the base and generally parallel to the bottom plate-facing surface of the base.

* * * * *